United States Patent
Ruegg et al.

(10) Patent No.: US 9,540,635 B2
(45) Date of Patent: Jan. 10, 2017

(54) BUFFER FOR ONE-STEP DNA EXTRACTION

(71) Applicant: Bio-Rad Laboratories, Inc., Hercules, CA (US)

(72) Inventors: Bryony Ruegg, San Francisco, CA (US); Ingrid Miller, Dixon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 203 days.

(21) Appl. No.: 13/889,520

(22) Filed: May 8, 2013

(65) Prior Publication Data

US 2013/0303746 A1 Nov. 14, 2013

Related U.S. Application Data

(60) Provisional application No. 61/644,553, filed on May 9, 2012.

(51) Int. Cl.
*C12N 15/10* (2006.01)
*C07H 21/04* (2006.01)

(52) U.S. Cl.
CPC ........... *C12N 15/1003* (2013.01); *C07H 21/04* (2013.01)

(58) Field of Classification Search
CPC ............................ C07H 21/04; C12N 15/1003
See application file for complete search history.

(56) References Cited

U.S. PATENT DOCUMENTS

| | | |
|---|---|---|
| 5,346,994 A | 9/1994 | Chomczynski |
| 5,792,651 A | 8/1998 | Colpan et al. |
| 5,945,515 A | 8/1999 | Chomczynski |
| 6,242,220 B1 * | 6/2001 | Wahle ............ C12N 15/1003 435/320.1 |
| 6,548,256 B2 | 4/2003 | Lienau et al. |
| 2004/0157223 A1 | 8/2004 | Lou et al. |
| 2006/0240409 A1 | 10/2006 | Prince et al. |

FOREIGN PATENT DOCUMENTS

| | | | |
|---|---|---|---|
| KR | 2002-0029476 A | | 4/2002 |
| WO | WO2011/083429 | * | 6/2011 ............ C12N 15/10 |
| WO | 2014/144174 A1 | | 9/2014 |

OTHER PUBLICATIONS

Chowdhury et al., "One step 'miniprep' method for the isolation of plasmid DNA" Nucleic Acids Research (1991) vol. 19 No. 10 p. 2792.*

Edwards et al.; "A simple and rapid method for the preparation of plant genomic DNA and PCR analysis"; *Nucl. Acids Res.;* 19(6):1349 (1991).

Kasajima et al.; "A protocol for rapid DNA extraction from *Arabidopsis thaliana* for PCR analysis"; *Plant Mol. Biol. Reporter;* 22:49-52 (2004).

Steiner et al.; "A rapid one-tube genomic DNA extraction process for PCR and RAPD analyses"; *Nucl. Acids. Res.;* 23(13):2569-2570 (1995).

International Search Report and Written Opinion from PCT/US2013/040081, mailed Sep. 30, 2013.

Hearn et al.; "DNA extraction techniques for use in education," *Biochemistry and Molecular Biology Education,* 38(3):161-166 (May 2010).

Wang et al.; "A simplified universal genomic DNA extraction protocol suitable for PCR"; *Genetics and Molecular Research;* 10(1):519-525 (Mar. 2011).

Extended European Search Report from EP. Appl. No. 13787594.4, mailed Dec. 8, 2015.

* cited by examiner

*Primary Examiner* — Eric Olson
(74) *Attorney, Agent, or Firm* — Kilpatrick Townsend & Stockton LLP

(57) ABSTRACT

DNA is extracted from epithelial cells and other cells without cell walls, by use of a DNA extraction buffer that contains a $C_1$-$C_4$ alcohol, a cell lysis detergent, and a buffering agent maintained at a slightly basic pH. The cells are immersed in the buffer and gently agitated at ambient temperature, and DNA extraction and precipitation occur in thirty minutes or less, and often in five minutes or less.

24 Claims, No Drawings

BUFFER FOR ONE-STEP DNA EXTRACTION

CROSS-REFERENCE TO RELATED PATENT APPLICATIONS

The present patent application claims benefit of priority to U.S. Provisional Patent Application No. 61/644,553, filed May 9, 2012, which is incorporated by reference.

BACKGROUND OF THE INVENTION

With the proliferation of studies involving DNA, laboratory procedures such as the polymerization chain reaction (PCR) and DNA sequencing have gained widespread use. Highly automated and efficient equipment and instrumentation have been developed for these procedures, but the DNA must first be extracted from biological cells, and this is one of the limiting factors in use of the procedures. With the ever-present goals of speed and low cost, there is a continuing need for new materials and procedures for extracting DNA in less time and with fewer opportunities for operator intervention and error.

SUMMARY OF THE DISCLOSURE

Epithelial cells and other cells that do not have cell walls are used in many DNA studies in view of the diversity of these cells, the many locations throughout the human body where they are found, and the roles that they play both in healthy physiological functions and in the proliferation of disease. It has now been discovered that DNA can extracted from these cells in a one-step procedure without the need for special conditions, long exposure times, costly chemicals, or specialized equipment, by using a DNA extraction buffer with as little as three ingredients in aqueous solution—a $C_1$-$C_4$ alcohol, a cell lysis detergent, and a buffering agent maintaining the pH of the solution within the approximate range of 7.5 to 9.0. Other ingredients may be included in certain embodiments of the invention, but are not generally needed. Included among these optional but unnecessary ingredients are, for example, in the substantial absence of proteases, reducing agents, and non-detergent inorganic salts.

These and other features, embodiments, and advantages of the invention will be apparent from the description that follows.

DETAILED DESCRIPTION OF SELECTED EMBODIMENTS

Of the $C_1$-$C_4$ alcohols that are suitable for inclusion in the DNA extraction buffers in the practice of this invention, examples are methanol, ethanol, and isopropanol, although other $C_1$-$C_4$ alcohols will also function effectively. Ethanol and isopropanol, either individually or together as a mixture, are of particular interest. The concentration of alcohol to which the cells are exposed can vary, but effective extraction will generally be obtained using an alcohol concentration of from about 50% to about 85%, and in many cases from about 60% to about 80%, all by weight.

Any of a wide range of cell lysis detergents can be used, including those that are denaturing, which are generally anionic or cationic, and those that are non-denaturing, which are generally either nonionic or zwitterionic. Examples of anionic detergents are sodium dodecyl sulfate (SDS), sodium octadecyl sulfate, sodium decyl sulfate, sodium n-dodecylbenzene-sulfonate, and lithium dodecyl sulfate. Examples of cationic detergents are trimethylhexadecylammonium chloride, 1-methyl-1'-tetradecyl-4,4'-bipyridinium dichloride, benzalkonium chloride, and benzyltrimethylhexadecylammonium chloride. Examples of nonionic detergents are pentaerythrityl palmitate, Triton X-100, NP-40, Brij-35, and Tween 20. Examples of zwitterionic detergents are 3[(3-cholamidopropyl)dimethylammonio]-1-propanesulfonate (CHAPS), 3-[(3-cholamidopropyl)dimethylammonio]-2-hydroxy-1-propanesulfonate (CHAPSO), and N-decyl-N,N-dimethyl-3-ammonio-1-propanesulfonate (Sulfobetaine). Denaturing detergents provide especially favorable results in many cases, and detergents that are either anionic or zwitterionic, particularly anionic, detergents, are of interest in many cases as well. Some of the more commonly used and highly convenient anionic detergents are sodium dodecyl sulfate (SDS), sodium octadecyl sulfate, and sodium decyl sulfate, particularly sodium dodecyl sulfate. The amount of detergent can vary within the scope of the invention, although in most cases an amount within the range of from about 0.05% to about 0.5% by weight will be the most efficient. In many cases, amounts within the range of 0.1% to about 0.2% by weight will be even more efficient.

Buffering can be achieved by use of any of a wide variety of buffering agents that will maintain the solution pH within the range stated above. Examples of suitable buffers are tris(hydroxy methyl)aminomethane (Tris), Tris-glycine, HEPES (N-2-hydroxyethyl-piperazine-N-2-ethanesulfonic acid), CAPS (3-(cyclohexylamino)-1-propanesulfonic acid), MES (2-(N-morpholino)-ethanesulfonic acid), Tricine (4-(2-hydroxyethyl)-1-piperazine propanesulfonic acid (EPPS), N-[tris(hydroxymethyl)-methyl] glycine), and combinations of these compounds. The concentration of the buffering agent may vary as well, although best results will often be obtained at concentrations of from about 3 mM to about 30 mM, or in many cases about 5 mM to about 20 mM, or about 6 mM to about 10 mM. A preferred pH range is about 7.8 to about 8.5.

For convenience, the DNA extraction buffer can be prepared as a concentrate to be added to an aqueous suspension of the cells from which the DNA is to be extracted. Such a concentrate may contain, for example, about 75% to about 90% by weight of the alcohol, about 0.1% to about 0.2% by weight of the detergent, and about 6 mM to about 10 mM of the buffering agent. The relative amounts of the aqueous cell suspension and the concentrate will largely be a matter of convenience and expediency, depending on the particular cells being used, and how and in what form the cells are obtained. In many cases, the volumetric ratio of cell suspension to concentrate will be within the range of about 1:1 to about 1:12, or about 1:2.5 to about 1:6.

One example of a DNA extraction buffer composition, which can also be used as a concentrate per the description above, is 8.33 mM Tris at pH 8.0, 0.167% SDS, and 83.33% isopropanol or ethanol:isopropanol at a 95:5 volume ratio (all percents by weight).

Among the advantages of the present invention are that DNA extraction using the DNA extraction buffers described above can be performed at mild temperatures, with no need for cooling or heating of the cells or the buffer. The procedure can thus be performed at normal room temperatures, such as in the range of 20-25° C., or more generally within the range of from about 15° C. to about 35° C., or at the temperature at which the cells are obtained. The procedure can also be performed without the use of numerous additional components that are commonly included in DNA extraction buffers and procedures of the prior art, or with substantially none of these components present. Examples of these components are proteases, reducing agents, and non-detergent, inorganic salts. These components can be included if desired, but successful and effective results can be obtained without their inclusion. The expression "substantially none" or "substantially no" as used herein to describe the amounts of proteases, reducing agents, and non-detergent, inorganic salts, means that any amounts that are present are either trace amounts, amounts included unintentionally, and/or amounts that do not significantly affect the rapidity or completeness of the DNA extraction.

Examples of proteases that are known for use in DNA extraction and not needed in the practice of this invention are serine proteases such as proteinase K, trypsin, chymotrypsin, elastase, subtilisin, streptogrisin, thermitase, aqualysin, plasmin, cucumisin, and carboxypeptidase A, D, C, or Y; cysteine proteases such as papain, calpain, or clostripain; acid proteases such as pepsin, chymosin, and cathepsin; and metalloproteases such as pronase, thermolysin, collagenase, dispase, aminopeptidases, and carboxypeptidase A, B, E/H, M, T, or U. Other known enzymes of similar utility will be apparent to those knowledgeable in DNA extraction, and are likewise not needed. In fact, no enzymes of any kind are needed in the DNA extraction buffer(s) described herein. Examples of reducing agents that are known for use in DNA extraction and not needed in the practice of this invention are dithiothreitol, β-mercaptoethanol, dithioerythritol, 2-aminoethanethiol, and 2-mercaptoethanol. Other known reducing agents of similar activity will be apparent to those knowledgeable in DNA extraction, and are likewise not needed. Examples of non-detergent, inorganic salts that are commonly used in DNA extraction and not needed in the practice of this invention are sodium chloride, sodium acetate, and potassium chloride. Here as well, other similar salts will be apparent to those knowledgeable in DNA extraction techniques, and are likewise not needed.

A further advantage of the use of the DNA extraction buffers described herein is that DNA extraction with these buffers can be performed in a one-step procedure in a relatively short period of time compared to corresponding procedures of the prior art. Thus, separate steps for cell lysis and for precipitation of the liberated DNA for example are not required; all such functions can be achieved by a single immersion of the cells in the DNA extraction buffer. Agitation may be useful in certain cases, but mild agitation such as swirling or gentle stirring will generally suffice. As noted above, the extraction can be performed at mild temperatures, including ambient temperature. Extraction and precipitation of the DNA with the use of the DNA extraction buffers herein can be achieved in as little as five seconds and less than thirty minutes, often less than fifteen minutes, and in many cases within a period of time ranging from about five seconds to about ten minutes, or from about five seconds to about five minutes. Once precipitated, the DNA can be recovered by conventional means, examples of which are decantation, centrifugation, filtration, and spooling (drawing DNA as a precipitate onto a rotating glass stirring rod).

The DNA extraction buffers and procedures described herein are useful for extracting DNA from cells without cell walls, tissues (e.g., muscle) or organs (e.g. hair follicles) comprising such cells, and whole organisms (e.g., nematodes), including both epithelial and non-epithelial cells and tissues, and mammalian (e.g., human), non-vertebrate, and insect cells, both from primary and secondary (e.g., tissue culture) sources. Other applicable cell and tissue types include but are not limited to epithelial, muscle, connective, and nervous tissues and include squamous, cuboidal, columnar, and pseudostratified epithelial cells, endothelial cells, mesothelial cells, fibroblasts, neurons, blood cells, muscle cells, and stromal cells. These cells can be found, for example, in the skin, the lungs, blood vessels, pericardium, stomach, and intestines, as well as in exocrine tissue, the pancreas, kidney tubules, the nasal and bronchia passages, the uterus, and the Fallopian tubes.

The following example is presented for illustrative purposes only.

EXAMPLE

An adult human subject gently chews his or her cheeks to loosen squamous epithelial cheek cells, then swishes common drinking water (such as tap water) in the mouth to collect the cells. The subject then transfers the water and cells from the mouth to a beaker. A DNA extraction buffer consisting of 8.33 mM Tris at pH 8.0, 0.167 weight % SDS, and either 83.33 weight % isopropanol or a denatured alcohol consisting of ethanol and alcohol at a 95:5 volume ratio (balance water) is then added to the beaker in a volumetric ratio of four parts of the buffer to one part of the cheek cell/drinking water suspension, and the resulting mixture is gently mixed and allowed to stand. In less than five minutes, the precipitated DNA is visible to the naked eye.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A process for extracting DNA from cells without cell walls, said process comprising:
   (a) immersing said cells in an aqueous solution comprising a C1-C4 alcohol at from about 50% to about 85% by weight, a cell lysis detergent at from about 0.05% to about 0.5% by weight, and a buffering agent maintaining a pH of from about 7.5 to about 9.0, and substantially no protease, substantially no reducing agent, and substantially no non-detergent, inorganic salt, at a temperature of from about 15° C. to about 35° C. for from about five seconds to about thirty minutes, to cause DNA to be liberated from said cells and to precipitate; and
   (b) recovering said DNA so precipitated from said aqueous solution.

2. The process of claim 1 wherein said C1-C4 alcohol is a member selected from the group consisting of methanol, ethanol, and isopropanol.

3. The process of claim 1 wherein said C1-C4 alcohol is isopropanol or a mixture of isopropanol and ethanol.

4. The process of claim 1 wherein said cell lysis detergent is a denaturing detergent.

5. The process of claim 1 wherein said cell lysis detergent is a member selected from the group consisting of anionic and zwitterionic detergents.

6. The process of claim 1 wherein said cell lysis detergent is an anionic detergent.

7. The process of claim 1 wherein said cell lysis detergent is a member selected from the group consisting of sodium dodecyl sulfate, sodium octadecyl sulfate, and sodium decyl sulfate.

8. The process of claim 1 wherein said cell lysis detergent is sodium dodecyl sulfate.

9. The process of claim 1 wherein said C1-C4 alcohol is a member selected from the group consisting of ethanol and isopropanol at a concentration of from about 60% to about 80% by weight, said cell lysis detergent is a member selected from the group consisting of sodium dodecyl sulfate, sodium octadecyl sulfate, and sodium decyl sulfate at a concentration of from about 0.1% to about 0.2% by weight, and said pH is from about 7.8 to about 8.5.

10. The process of claim 1 wherein said process consists of combining an aqueous suspension of said cells with a cell lysis buffer consisting of ethanol, isopropanol, or a mixture of ethanol and isopropanol, at a concentration of from about 75% to about 90% by weight, sodium dodecyl sulfate at a concentration of from about 0.1% to about 0.2% by weight, and said buffer is a member selected from the group consisting of tris(hydroxymethylamino)-methane at concentration of from about 6 mM to about 10 mM and a pH of from about 7.8 to about 8.5, balance water, in the total absence of any protease, reducing agent, or non-detergent, inorganic salt.

11. The process of claim 10 wherein said aqueous suspension and said cell lysis buffer are combined at a suspension:buffer volumetric ratio of from about 1:1 to about 1:12.

12. The process of claim 10 wherein said aqueous suspension and said cell lysis buffer are combined at a suspension:buffer volumetric ratio of from about 1:2.5 to about 1:6.

13. The process of claim 1 wherein step (a) is performed for a period of time ranging from about five seconds to about ten minutes.

14. The process of claim 1 wherein step (a) is performed for a period of time ranging from about five seconds to about five minutes.

15. A DNA extraction buffer comprising:
(i) a C1-C4 alcohol at a concentration of from about 75% to about 90% by weight,
(ii) a DNA extraction detergent at a concentration of from about 0.05% to about 0.5% by weight, and
(iii) a buffering agent maintaining a pH of from about 7.5 to about 9.0,
in aqueous solution containing substantially no protease, substantially no reducing agent, and substantially no non-detergent, inorganic salt.

16. The DNA extraction buffer of claim 15 wherein said C1-C4 alcohol is a member selected from the group consisting of methanol, ethanol, and isopropanol.

17. The DNA extraction buffer of claim 15 wherein said C1-C4 alcohol is isopropanol.

18. The DNA extraction buffer of claim 15 wherein said DNA extraction detergent is a denaturing detergent.

19. The DNA extraction buffer of claim 15 wherein said DNA extraction detergent is a member selected from the group consisting of anionic and zwitterionic detergents.

20. The DNA extraction buffer of claim 15 wherein said DNA extraction detergent is an anionic detergent.

21. The DNA extraction buffer of claim 15 wherein said DNA extraction detergent is a member selected from the group consisting of sodium dodecyl sulfate, sodium octadecyl sulfate, and sodium decyl sulfate.

22. The DNA extraction buffer of claim 15 wherein said DNA extraction detergent is sodium dodecyl sulfate.

23. The DNA extraction buffer of claim 15 wherein said C1-C4 alcohol is a member selected from the group consisting of ethanol and isopropanol at a concentration of from about 60% to about 80% by weight, said DNA extraction detergent is a member selected from the group consisting of sodium dodecyl sulfate, sodium octadecyl sulfate, and sodium decyl sulfate at a concentration of from about 0.1% to about 0.2% by weight, and said pH is from about 7.8 to about 8.5, and said composition is devoid of proteases, reducing agents, and non-detergent, inorganic salts.

24. The process of claim 1, wherein the aqueous solution lacks any protease or reducing agent.

\* \* \* \* \*